United States Patent [19]
Laffler et al.

[11] Patent Number: 5,858,652
[45] Date of Patent: Jan. 12, 1999

[54] DETECTION AND AMPLIFICATION OF TARGET NUCLEIC ACID SEQUENCES

[75] Inventors: Thomas G. Laffler, Libertyville; Stanley R. Bouma, Grayslake, both of Ill.; Uwe Spies, Linden, Germany

[73] Assignee: Abbott Laboratories, Abbott Park, Ill.

[21] Appl. No.: 331,298

[22] Filed: Oct. 28, 1994

Related U.S. Application Data

[63] Continuation of Ser. No. 166,272, Dec. 13, 1993, abandoned, which is a continuation of Ser. No. 48,561, Apr. 14, 1993, abandoned, which is a continuation of Ser. No. 747,580, Aug. 19, 1991, abandoned, which is a continuation-in-part of Ser. No. 394,051, Aug. 17, 1989, abandoned, which is a continuation-in-part of Ser. No. 239,649, Aug. 30, 1988, abandoned.

[51] Int. Cl.$^6$ ............................... C12Q 1/68; C12P 19/34
[52] U.S. Cl. ............................................. 435/6; 435/91.2
[58] Field of Search ........................................ 435/6, 91.2

[56] References Cited

U.S. PATENT DOCUMENTS

| | | | |
|---|---|---|---|
| 4,581,333 | 4/1986 | Kourilsky et al. | 435/6 |
| 4,605,735 | 8/1986 | Miyoshi et al. | 536/27 |
| 4,626,501 | 12/1986 | Landes . | |
| 4,670,379 | 6/1987 | Miller . | |
| 4,683,195 | 7/1987 | Mullis et al. | 435/6 |
| 4,683,202 | 7/1987 | Mullis | 435/91 |
| 4,965,188 | 10/1990 | Mullis et al. | 435/6 |

FOREIGN PATENT DOCUMENTS

| | | |
|---|---|---|
| 0 097 373 | 1/1984 | European Pat. Off. . |
| 0097373 | 4/1984 | European Pat. Off. ........ C07H 21/00 |
| 0230363 | 7/1987 | European Pat. Off. . |
| 0 237 362 | 9/1987 | European Pat. Off. . |
| 0237362 | 9/1987 | European Pat. Off. .......... C12Q 1/68 |
| 0 370 694 | 5/1990 | European Pat. Off. . |
| 0 371 437 | 6/1990 | European Pat. Off. . |
| 0 374 665 | 6/1990 | European Pat. Off. . |
| 2 169 403 | 7/1986 | United Kingdom . |
| 2 202 328 | 9/1988 | United Kingdom . |
| 87/05942 | 10/1987 | WIPO . |
| 89/09281 | 10/1989 | WIPO . |
| WO 90/06374 | 6/1990 | WIPO . |
| WO 90/11369 | 10/1990 | WIPO . |
| WO 90/11372 | 10/1990 | WIPO . |
| WO 90/12115 | 10/1990 | WIPO . |

OTHER PUBLICATIONS

Kemp, et al. Proceedings National Academy of Science, 86:2423–2427 (Apr. 1989).
Caskeys *Science,* 236:1223–1229 (Jun. 1987).
Langer et al, Proc. Natl. Acad. Sci. USA, V. 78, Nov. 1981, pp. 6633–6637.
Mullis et al Cold Spring Harbor Symposia on Quantitative Biology vol. LI (1986).
Cold Spring Harbor Press; Cold Spring Harbor, NY pp. 263–273.
Landegren et al. Science 241:pp. 1077–1079 (26 Aug. 1988).

*Primary Examiner*—Stephanie W. Zitomer
*Assistant Examiner*—Ethan Whisenant
*Attorney, Agent, or Firm*—Thomas D. Brainard; Paul D. Yasger

[57] ABSTRACT

A method and kits for amplifying and detecting target nucleic acid sequences in a sample is disclosed. The method employs primers which have reactive pair members linked to them. The reactive pair members can be attached to a solid phase and/or detected by labeled conjugate.

40 Claims, 10 Drawing Sheets

DOUBLE STRANDED
TARGET SEQUENCE

DENATURE, AND
ANNEAL CAPTURE
PRIMER

SYNTHESIZE
EXTENSION PRODUCTS

+

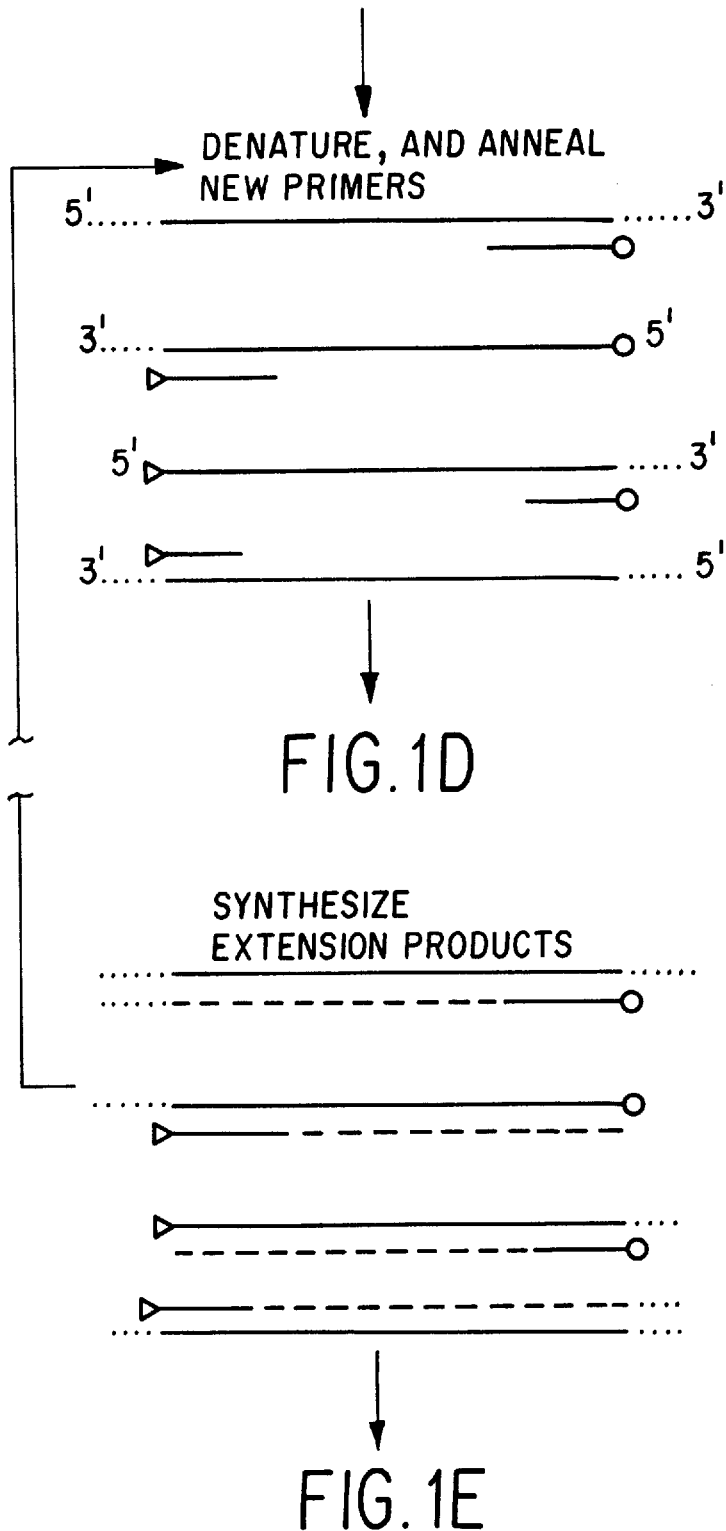

PRODUCTS
TO BE
DETECTED

SOLID PHASE
SEPARATOR

MICROPARTICLES

DETECTION WITH
DETECTABLE LABEL

DOUBLE STRANDED
TARGET SEQUENCE

DENATURE, AND
ANNEAL PRIMARY
PRIMERS

SYNTHESIZE PRIMARY
EXTENSION PRODUCTS

DENATURE, AND ANNEAL
PRIMARY PRIMERS

DOUBLE-STRANDED
TARGET SEQUENCE

↓

DENATURE AND ANNEAL PRIMERS
(▷ = MEMBER OF REACTIVE GROUP,
○ = DETECTABLE GROUP e.g. FLUOROPHORE)

↓

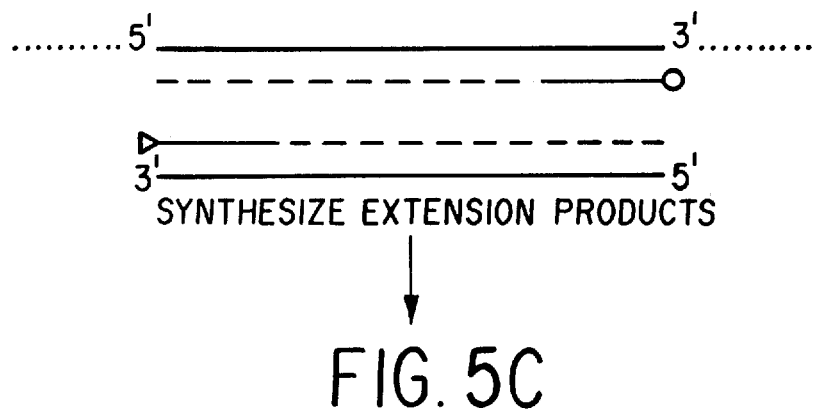
SYNTHESIZE EXTENSION PRODUCTS
FIG. 5C
DENATURE, REANNEAL, REEXTEND (MANY TIMES)
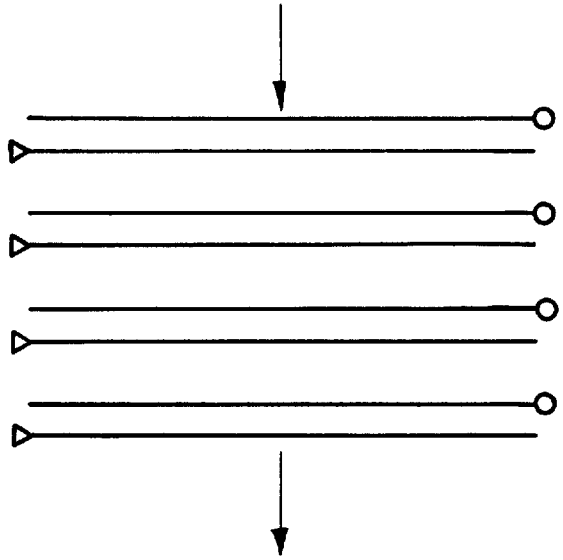
FIG. 5D
CAPTURE TO SOLID PHASE, WASH AWAY UNBOUND MATERIAL, DETECT SIGNAL
FIG. 5E

DETECTION AND AMPLIFICATION OF TARGET NUCLEIC ACID SEQUENCES

This application is a continuation of U.S. Ser. No. 08/166,272, Dec. 13, 1993 (now abandoned); which is a continuation of U.S. Ser. No. 08/048,561, filed Apr. 14, 1993 (now abandoned); which is a continuation of U.S. Ser. No. 07/747,580 filed Aug. 19, 1991 (now abandoned); which is a continuation-in-part of U.S. Ser. No. 07/394,051, Aug. 17, 1989 (now abandoned); which is a continuation-in-part of U.S. Ser. No. 07/239,649, filed Aug. 30, 1988 (now abandoned).

BACKGROUND OF THE INVENTION

1. Field of the Invention

This invention relates to a method for detecting and amplifying a target nucleic acid sequence in a sample. In particular, this invention relates to a polymerase chain reaction which is amenable to automation. With a polymerase chain reaction (PCR), one can "amplify" (i.e., increase the number of) target oligonucleotide molecules in a sample to be analyzed for the presence of that target sequence.

2. Description of Related Art

One type of polymerase chain reaction is disclosed in U.S. Pat. Nos. 4,683,202 and 4,683,195 which are incorporated herein by reference. In this type of polymerase chain reaction, two complementary polynucleotide strands are amplified by treating the strands with two oligonucleotide primers such that an extension product of each primer is synthesized which is complementary to each nucleic acid strand. The primers are selected such that the extension product of one primer forms a template for the synthesis of an extension product from the other primer once the extension product of the one primer is separated from the template. A chain reaction is maintained by a cycle of denaturing the primer extension products from their templates, treating the single-stranded molecule generated with the same primers to re-anneal, and allowing the primers to form further extension products. The cycle is repeated for as many times as it takes to increase the target nucleic acid segments to a concentration where they can be detected.

Typically, the amplified target sequence is detected by denaturing the double-stranded products formed by PCR, and treating those products with one or more reporter probes which hybridize with the extension products. The reporter probe has a detectable label, and is usually added in excess. The unhybridized reporter probe, therefore, must be separated from the hybridized reporter probe requiring a separation step. In another method of detecting the extension products without reporter probe and a separation step, the extension products are detected by gels stained with ethidium bromide.

Regardless whether reporter probes or gels are used, prior PCR methods are quite difficult to automate. Using reporter probes requires denaturing the extension products, annealing the reporter probe, and in some cases separating excess reporter probe from the reaction mixture. Using gels, of course, is time consuming, labor intensive, and thus impractical to automate if rapid results are desired.

SUMMARY OF THE INVENTION

The present invention is a method and kit for amplifying and detecting target nucleic acid sequences. The method involves hybridizing to each of the target and its complementary strand an oligonucleotide primer conjugated to a member of a reactive pair. In the presence of target, an extension product complementary to each nucleic acid strand is synthesized from each primer, the extension product of each primer forming a template for the synthesis of further extension products from the other primer once the extension product is separated from its complement. The primer extension products are separated from the templates on which they were synthesized to produce single-stranded molecules. The single-stranded molecules are treated with the primers under conditions that a primer extension product is synthesized using each of the single strands produced as templates to form further double-stranded products. The double stranded products are captured on a solid phase having immobilized thereon the other member of one of the reactive pairs associated with the primer so that the double-stranded products become linked to the solid phase by the one reactive pair. Before, during or after the solid phase capture step, the double stranded products are treated with the other member of the other reactive pair labeled with a detectable moiety whereby the double-stranded products are labeled with the detectable moiety. The detectable moiety associated with said solid phase is then detected to indicate whether any target was present in the original sample.

This method, therefore, provides an easy separation step using a solid phase whereby the labeled extension products can be separated from the reaction mixture at the same time that the bound label is separated from any unbound label.

The current invention also involves kits for performing DNA probe assays, which kits include primers at least one of which has a first reactive pair member linked thereto as well as solid phase materials having linked thereto a second reactive pair member reactive with the first reactive pair member.

BRIEF DESCRIPTION OF THE DRAWINGS

FIG. 1A, 1B, 1C, 1D, 1E, 1F, 1G and 1H are a schematic of a first embodiment of the present invention where two primers are employed, each of which is linked to a member of a reactive pair.

FIG. 5A, 5B, 5C, 5D and 5E are a schematic of a fifth embodiment of the present invention employing two primers, one being linked to a member of a reactive pair, the other being linked to a detectable moiety;

DETAILED DESCRIPTION OF THE INVENTION

Figure 1A:
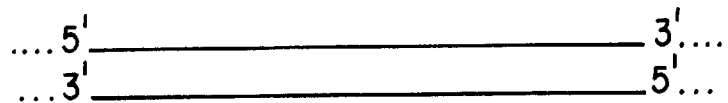
Figure 1B:
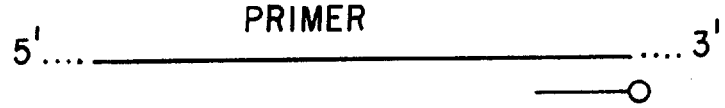
Figure 1B:
Figure 1C:
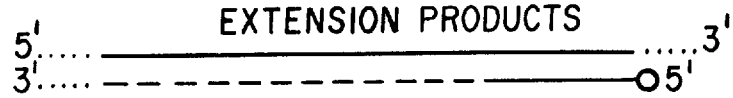
Figure 1C:
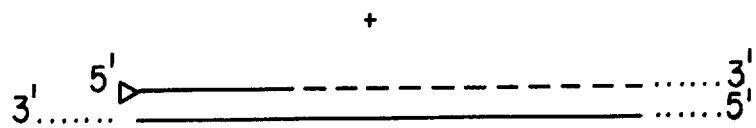
Figure 1F:
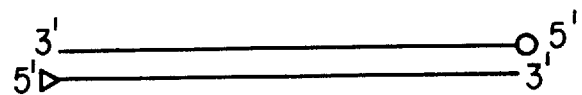
Figure 1F:
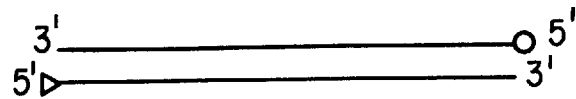
Figure 1G:
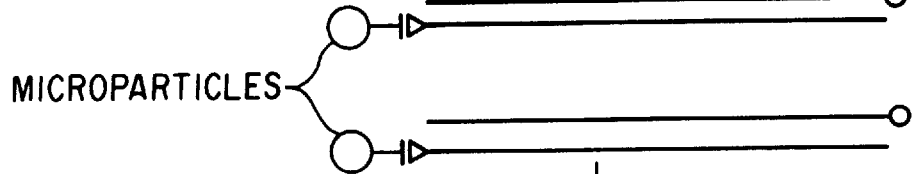
Figure 1H:
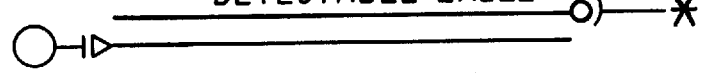
Figure 1H:
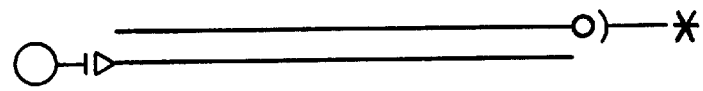
Figure 2A:
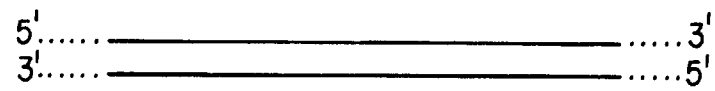
FIG. 2A, 2B, 2C, 2D, 2E and 2F are a schematic of a second embodiment of the present invention where two pairs of primers, one pair "nested" within the other, are used, the nested pair each having a reactive pair member linked thereto.
Figure 2B:
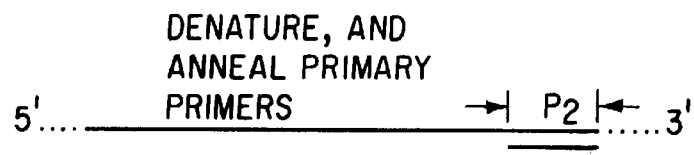
Figure 2C:
Figure 2C:
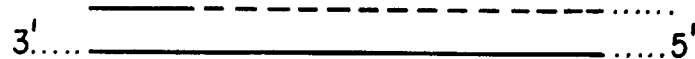
Figure 2D:
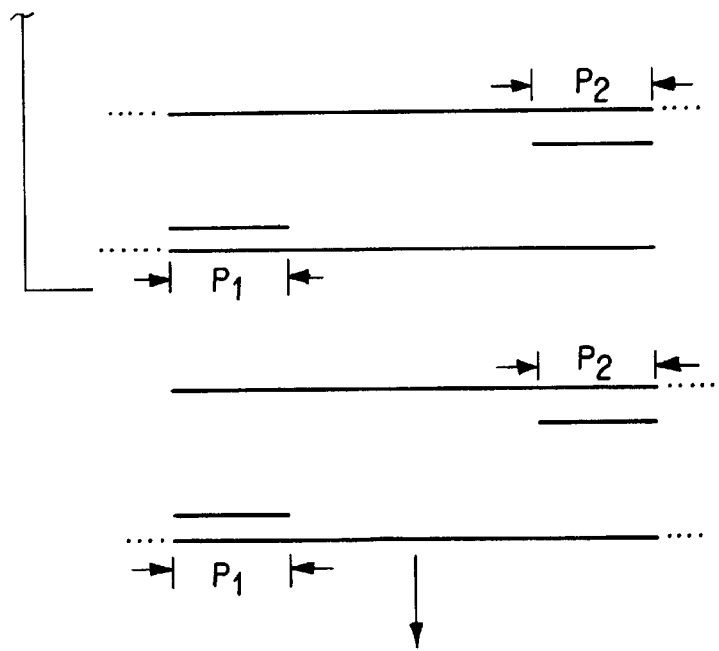
Figure 2E:
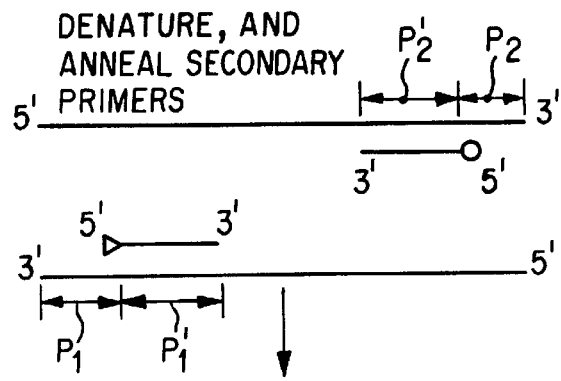
Figure 2F:
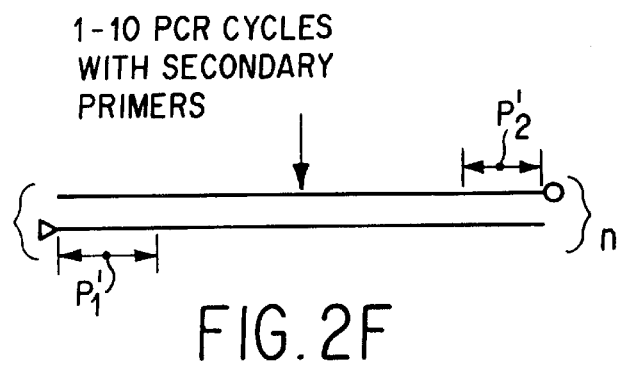

The current invention involves a polymerase chain reaction (PCR) using "capture" oligonucleotide primers each of which is conjugated to a member of a reactive pair. In FIG. 1, a double-stranded target sequence is denatured (step A), and capture primers are annealed to the 3' end of each of the original target sequences (step B). It is important that the capture primers be of a length which does not permit one capture primer to hybridize with portions of the target nucleotide strand complementary to the other capture primer. The capture primers are each linked or conjugated at their 5' ends to a member of a reactive pair (defined below), each member being illustrated graphically by a circle or a triangle. While apparently not essential to this invention, the presence of a reactive pair at the 5' end has the additional effect of blocking any degradative reaction of 5'-3' exonucleolytic activity.

Primer extension products are then synthesized using a DNA polymerase to extend the 3' end of each of each primer (step C). The extension products are then separated from their templates by denaturing the double-stranded products of step C, and new primers are annealed to the extension products of step C (see step D). Additional extension products are then synthesized (step E). Step D is repeated using the double-stranded products of step E for as many cycles as is necessary to increase the concentration of target sequence to a level where it can be detected.

When the PCR is completed, double stranded products (step F), each strand of which has a member of a reactive pair at its 5' end represented by circles and triangles, will predominate in the reaction mixture.

Suitable reactive pair members include covalent and non-covalent reactive pairs. Suitable non-covalent reactive pairs include typical ligand-antiligand members such as antibody and antigen, biotin and avidin, enzyme and enzyme receptor, carbohydrate and lectin, enzyme and enzyme cofactors, and a pair of complementary DNA strands. It is preferred that the reactive pairs be selected from specific binding members, i.e., those members which have a non covalent specificity for one another (e.g. biotin and avidin, or antibody and antigen, or the like). Suitable covalent reactive pairs include a free thiol (attached to the 5' end of each primer) which reacts with heavy metals such as lead or mercury (attached to the solid phase or label).

The products to be detected (step F) are separated from the reaction mixture by reacting one of the reactive members (e.g., represented by the triangles) with the second member reactive or complementary with it, where the second member is conjugated or linked to a solid phase such as the microparticles shown. With the extension products attached to a solid phase, the extension products can be separated from the reaction mixture by filtering or passing through the $IM_x$® analyzes disposable reaction cell sold by Abbott Laboratories.

Other solid phases can also be used. For instance, the second member can be directly linked to a medium (e.g., a membrane or filter), and the extension products passed through the medium and captured directly on it. Beads or columns can also be used in conventional solid phase separation techniques to remove the extension products from the reaction mixture, provided of course, the beads or column have the second member of the reactive pair linked thereto.

Before, during or after solid phase separation, the other reactive pair member (e.g., represented by the circle) is reacted with the second member of its reactive pair specific to it, where the second member is labeled with a detectable label as defined below. As can be seen (step H), a conjugate is formed with two complementary oligonucleotide strands each of which has at its 5' end a reactive pair member (preferably a specific binding member) which is linked via the other member of the reactive pair to either a label or a solid phase. The excess label/reactive pair member conjugate member is separated from bound label preferably by filtration using the microparticles linked to the opposite end of the DNA strand.

Once the solid phase is separated from the solution, any label associated with the solid phase indicates that primer extension products were formed using the original target nucleic acid sequence as a template. In the absence of target sequence, no extension products would be formed and the double stranded complex of step H would not be possible.

The present method of PCR is easy to automate. With oligonucleotide capture primers—each of which is conjugated to a member of a reactive pair—primers can be processed to amplify the target sequence using conventional techniques. However, once the double-stranded products (step F) are formed, no denaturation and addition of a reporter DNA probe is necessary. The extension products can be left double-stranded, can be detected with a labeled reactive member, and separated (before, during or after detection) with a reactive member conjugated to a solid phase.

Preferably, the reactive member on one capture primer is different from the reactive member on the other capture primer. Most preferably, the two reactive members are selected from different pairs of reactive members. For instance, where the reactive member on the primer reactive with the solid phase conjugate is biotin (the solid phase conjugate including avidin or anti-biotin), the reactive member on the other primer to be conjugated with the label could be a hapten or an antigen which is reactive with a labeled antibody. Thus, the labeled reactive member will not cross react with the solid phase conjugate, and the reactive members at each end of the amplified products (step F) will not react with each other.

Alternatively, the reactive pair members conjugated or linked to each capture primer can be the same. While this configuration may be more useful in agglutination-type assays, it is less desirable for solid phase capture configurations, since it is more difficult to ensure that the double stranded complex will attach to both solid phase and label conjugate.

The method of linking or conjugating a reactive pair member to a DNA primer depends, of course, on the type of reactive pair member used. However, the linkage preferred will be a covalent bond through the 5' hydroxyl group. In one procedure, a primary aliphatic amine is added to the 5' hydroxyl of the oligonucleotide during primer synthesis via phosphoramidite chemistry. Subsequently, this amine is reacted with a hapten species (e.q. fluorescein isothiocyanate, or biotin-N-hydroxysuccinimide ester) to yield a primer linked to a reactive pair member.

Extension products are formed by exposing the primers annealed to their templates to a DNA polymerase, preferably a temperature stable DNA polymerase such as the Taq polymerase disclosed in European Patent Specification 258,017. The DNA polymerase will, of course, copy the template strand synthesizing DNA from the primers in the 5' to 3' direction. Temperature stable polymerases are preferred because the preferred way of denaturing the double stranded extension products is by exposing them to a high temperature (e.g. about 95 degrees centigrade) during the PCR cycle as disclosed in U.S. Pat. No. 4,683,202. However, if different methods of denaturing the extension products are used, other DNA polymerases or fragments thereof may be employed, including a Klenow fragment.

This invention can also be practiced with "nested" primers (FIG. 2). A double-stranded target sequence (step A, FIG. 2) is denatured, and "primary" primers are annealed to the single strands in the target region of interest. The primary primers hybridize to regions $P_2$ and $P_1$ at the 3' ends of the respective target strands. Using PCR, primary extension products are then synthesized (step C) and the process is repeated to obtain the desired degree of amplification. It is to be recognized that it does not matter how the target is first amplified in this embodiment and any method of amplification will suffice for this step.

Once the desired degree of amplification with the primary primers is complete, secondary primers (step E, FIG. 2) are annealed to the primary extension products produced in steps A–D. The secondary primers are "capture" primers and have at their 5' ends members of reactive pairs as defined above. The secondary primers are synthesized so as to hybridize at regions on their respective strands near or adjacent (but not overlapping) where the 3' terminus of the primary primers would be if hybridized to the same strands. It can be seen in step E, for instance, a first secondary primer hybridizes to a sequence $P_1'$ which is adjacent the sequence $P_1$ where the first primary primer would hybridize if it were in solution with the secondary primers. A second secondary primer hybridizes at a region $P_2'$ adjacent the region $P_2$ where the second primary primer would hybridize if it were in solution.

One or more, preferably one to ten PCR cycles are performed with the secondary (capture) primers to produce double-stranded extension products (step F, FIG. 2) which have reactive pair members at each end of the double-stranded molecules. These double-stranded molecules can then be detected with label conjugates and separated with solid phase conjugates as previously described.

The advantage of using nested primary and secondary primers is improved specificities. Secondary extension products will not be synthesized unless the secondary primers hybridize to the primary extension products. Thus, in the event that the primary primers hybridize to a nucleic acid sequence other than the target desired, the secondary primers will not hybridize to the actual primary extension products. The secondary extension products-will only be formed if the proper primary extension products are synthesized. Accordingly, the specificity can be improved if the secondary primers are added to the reaction mixture for one or more, preferably one to ten PCR cycles to produce a detectable concentration of secondary extension products.

Figure 3:
FIG. 3 is a schematic of a third embodiment of the present invention where three primers are employed, one primer nested within the other two.
Figure 3:
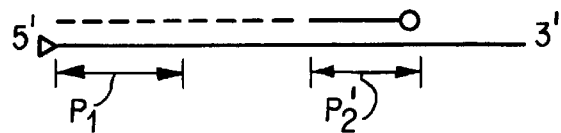

Instead of a pair of nested secondary primers, a single nested secondary primer can be employed (FIG. 3) where a first pair of primers ($P_1$ and $P_2$) are employed to form primary extension products. One of the primary primers ($P_1$) is a "capture" primer (ie. is linked to a member of a first reactive pair), whereas the other primary primer ($P_2$) is not. A secondary "capture" primer $P_2'$ (having a member of a second reactive pair at its 5' end) hybridizes to the primary extension products at a site near or adjacent (but not overlapping) the site where the 3' terminus of primer $P_2$ would hybridize if it were still in solution. A secondary extension product is formed using $P_2'$ so that a double-stranded oligonucleotide sequence is formed having reactive pairs at the 5' ends of both the individual strands. (One reactive pair member comes from the primary primer and the other comes from the secondary primer.)

Figure 4:
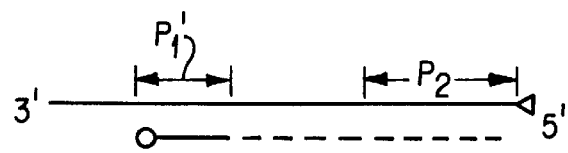
FIG. 4 is a schematic of a fourth embodiment of the present invention where two pairs of "nested" primers are employed, one pair having one member of one reactive pair linked thereto, the other pair having one member of a second reactive pair linked thereto.
Figure 4:
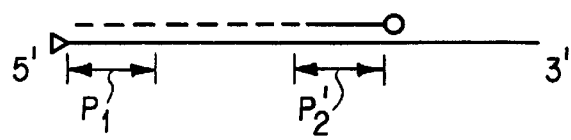

Alternatively, the primary primers ($P_1$ and $P_2$, FIG. 4) can be linked with the same first member of a first reactive pair and the secondary primers $P_1'$ and $P_2'$ can be linked with a first member of a second reactive pair different from the first reactive pair. Thus, when secondary extension products are formed, hybrids such as those shown in FIG. 4 having reactive pair members at the 5' ends at each strand are formed which can be separated by solid phase separation and labeled as described above. Although this embodiment is a plausible configuration, it has not been found to provide results as good as the other configurations and, therefore, is less preferred.

Figure 5A:
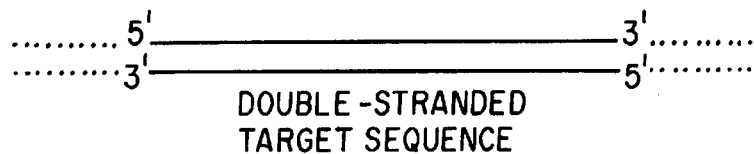
Figure 5B:
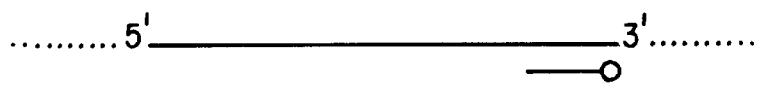
Figure 5B:
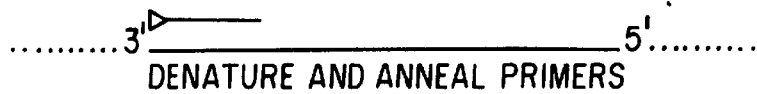

A fifth embodiment of this invention is illustrated in FIG. 5. The double stranded target (Step A) is denatured, and a pair of primers are annealed to the strands according to the procedures described above. However, one of the primers has linked to its 5' end a directly detectable label represented by the symbol "Ⓗ". The other primer has linked to its 5' end a member of a reactive pair as before. Extension products are synthesized (Step C), and the PCR process is repeated as many times as necessary (Step D, FIG. 5) to obtain the desired degree of amplification. After amplification, the double stranded extension products are captured on a solid phase (e.g. the microparticle shown in Step E, FIG. 5) which has the other member of the reactive pair (reactive with the reactive pair member on the extension products). Thus, the capture and direct detection can be accomplished simply by using one primer bearing a reactive pair member and the other primer bearing a detectable label directly attached to it.

In this fifth embodiment, it is preferred to employ a chemiluminescent or fluorescent label. The direct linkage of a chemiluminescent label to the primer can be accomplished by reacting the 5' hydroxy of the one primer during primer synthesis to a primary aliphatic amine via phosphoramidite chemistry. The primer with the amine can then be reacted with an acridinium active ester to link the acridine to the primer. The primer can also be linked directly to a fluorophore as described in Example 6 below. Either primer can then be used in PCR as described above.

Besides chemilumophores, other detectable labels can be employed including chromophores and fluorophores provided the label can survive the temperature cycling required in the PCR process.

The reactants employed in this invention can be provided in kit form to the user. The kit includes primers (at least one of which is linked with a member of a reactive pair), a DNA polymerase, and a solid phase having the other member of the reactive pair. If the first embodiment of this invention is to be practiced, the kit would include two primers, each of which is linked to members of different reactive pairs, a detectable label-reactive pair member conjugate, and the solid phase conjugate and polymerase described above. If the second or fourth embodiments are to be practiced, the kit would include two pairs of "nested primers" where at least one primer has a member of a reactive pair linked to it which member can bind to another reactive pair member linked to a solid phase also provided in the kit with DNA polymerase. If the third embodiment is to be practiced only one nested primer will be provided which primer has a reactive pair member linked to it. Finally, if the fifth embodiment is to be practiced, the kit would include two primers, one of which is linked directly to a detectable label and the other of which is attached to a member of a reactive pair. The kit would include a solid phase/reactive pair member conjugate and DNA polymerase.

In one variation of the method and/or kit of the invention, the primers are specially selected to have a characteristic property; namely, the 3' terminus of one primer hybridizes at a position substantially opposite the position (on the opposing strand) at which the 3' terminus of the other primer hybridizes. After several cycles of PCR, the predominant "short products" are species consisting of one primer and an extension which is substantially the complement of the other primer. This is referred to herein as "short" PCR products, since the amplicon is only as long as the two primers and shares the sequence information of the two primers.

A preferred variation of short PCR utilizes primers that each have 3' termini one base short of the other on their respective strands; which is to say that the 3' hydroxyls of the two primers would be at directly opposing positions on the strands when the strands are aligned. In other words, the first base in the extension of either primer is the complement of the 3' terminus of the other primer. In this configuration, the primers are synthesized from one continuous known sequence of target DNA, approximately half of the sequence being used for each primer, taking care to use the sequence of the complement for one of the primers.

In diagnostic applications, it is preferable to employ primers of sufficient length to insure specificity. Generally, primers having from about 15 to about 50 nucleotides are used, more usually from about 20 to 40. Consequently, the predominant "short product" comprises from 30 to 100, more usually 40 to 80 nucleotides in length. This is in contrast to conventional PCR, which typically amplifies larger regions to generate products having from 100 to several thousand or more nucleotides, including sequences not complementary to the primers.

One advantage associated with short PCR is its ability to detect target DNA which is old and fragmented, or otherwise deteriorated or otherwise degraded. Since a shorter target is employed, there is a greater likelihood that the target will remain intact in all forms of degraded DNA.

Another advantage occurs when each primer is labeled at its 5' end with a distinct specific binding ligand or other reactive pair member. After multiple cycles, each short PCR product, when duplexed with its complementary short PCR product, has differentiable specific binding ligands attached at each end of the duplex. This short, bivalent molecule can easily be detected in standard sandwich immunoassay formats, such as those discussed above.

The invention will now be further described by the following examples The examples are illustrative only and shall not be construed as limiting the invention in any way.

Example 1

Oligonucleotide Synthesis.

Polymerase Chain Reaction (PCR) primers designated A through G (see Table 1 below) were synthesized on an Applied Biosystems 380B DNA synthesizer using β-cyanoethylphosphoramidites. The couplings were performed with wait times of 30 sec, in order to maximize coupling yields. After the oligonucleotide chain synthesis was complete, Aminomodifier II° (Clontech, Palo Alto, Calif.) was added in the last cycle to give, upon oxidation and deprotection, a primary amine-terminated oligonucleotide chain.

Example 2

Oligonucleotide Labeling

The PCR primers from Example 1 were linked with a member of a reactive pair essentially following the protocol of Urdea, et. al. [Nucleic Acids Research 16(11) 4937–4956 (1988)].

TABLE 1

| | Reactive Pair Member | Sequence |
|---|---|---|
| A | none | 5'-AAAATTCGCAGTCCCCAACCTCCAATCACTCACCA-3' |
| B | none | 5'-GCGGTATAAAGGGACTCACGATGCTGTACAGACTT-3' |
| C | F1* | 5'-NH$_2$—TTGTCCTGGTTATCGCTGGATGTGTCTGCGGCGTT-3' |
| D | F1* | 5'-NH$_2$—CTTCATCCTGCTGCTATGCCTCATCTTCTTATTGG-3' |
| E | Biotin | 5'-NH$_2$—AGGGAAACTTAGAGTTGCCTTGAGCAGGAGTCGTG-3' |
| F | Biotin | 5'-NH$_2$—GCGGTATAAAGGGACTCACGATGCTGTACAGACTT-3' |
| G | none | 5'-TTGTCCTGGTTATCGCTGGATGTGTCTGCGGCGTT-3' |

*Where F1 = fluorescein.

Where fluorescein is the member of a reactive pair (ie. primers C and D), sense primers (5'—NH$_2$—TTGTCCTGGTTATCGCTGGATGTGTCTGCGGCGTT-3' and 5'—NH$_2$—CTTCATCCTGCTGCTATGCCTCAT CTTCTTATTGG-3') were treated with 2 mg of fluorescein isothiocyanate in 100 µL of sodium borate buffer, pH 9.0, at room temperature for 15 hours. The excess fluorescein was removed by passage of the reaction mixture through a NAP-5 column (Pharmacia, Piscataway N.J.) which had been equilibrated with 10 mL of water. The solvent was removed from the eluate in vacuo, and the yellow residue was taken up into 150 µL formamide. The fluoresceinated oligonucleotide was purified by gel electrophoresis (12% polyacrylamide/8M urea) on a slab gel (0.15×40 cm) at 40 Watts constant power. After identification of the fluoresceinated band by UV shadowing, the primer was excised and extracted from the gel using 0.1M TRIS, 0.5M NaCl, 5 mM EDTA, at 60° C. for 16 hours.

Where biotin is the member of a reactive pair: (ie. primers E and F), antisense primers (5'—NH$_2$—AGGGAAACTTAGAGTTGCCTTGAGCAGGAGTC GTG-3' and 5'—NH$_2$—GCGGTATAAAGGGACTCACG ATGCTGTACAGACTT-3') were dissolved in 100 µL of 0.1M sodium phosphate buffer, pH 7.5, and treated with 2 mg biotin-(aminocaproyl)$_2$-N-hydroxysuccinimide ester in 100 µL dimethylformamide (DMF) for 16 hours at room temperature. These primers were purified by gel filtration and electrophoresis as described above for the fluorescein-labeled oligonucleotides.

Example 3

A Single Pair of Capture Primers

Two reactions containing 1 µL of a DNA solution with either 0 or $10^5$ hepatitis B virus (HBV) plasmid DNA molecules per μL was used as a target for 30 cycles of PCR with primers D and F (see Table 1, as prepared in example 2 with reactive pair members) in a buffer containing 10 mM Tris pH 8.3, 50 mM KCl, 2.5 mM $MgCl_2$, 200 μM of each deoxyribonucleotide triphosphate (dNTP), 0.01% gelatin, and 1.25 units of $T_{aq}$ DNA polymerase. The final oligonucleotide concentration was 0.1 μM each. Each sample was overlayed with a small volume of mineral oil. Samples were heat denatured at 94° C. for 5 minutes prior to cycling. Each PCR cycle consisted of a 1 min. denaturation step at 94° C.; a 2 min, annealing step at 50° C.; and a 2 min. extension step at 72° C. Reaction volume was 50 μL. The amplified DNA product was 392 base pairs (bp) as determined by the physical location of the two primer sequences within the HBV surface antigen gene. The double labeled DNA products with reactive pair members at each end were detected by a microparticle immunoassay performed on a prototype of the Abbott $IM_x$® analyze system using anti-fluorescein coated microparticles and an anti-biotin:alkaline phosphatase detection conjugate. The result was:

| No. of molecules | Signal |
| --- | --- |
| 0 | 51.0 |
| $10^5$ | 323.8 |

Example 4

Nested Pairs of Primary and Secondary Primers

Six reactions containing 1 μL of a stock DNA solution with either 0, $10^2$, $10^3$, $10^4$, $10^5$, $10^6$ HBV plasmid DNA molecules per μL was used as a target for 30 cycles of PCR using the HBV surface antigen gene specific primary oligonucleotide primers A and B. PCR reaction conditions were identical to those described in Example 3 except that the final oligonucleotide concentration was 1 μM each. The amplified DNA product was 492 base pair (bp) as determined by the physical location of the two primer sequences within the HBV surface antigen gene.

After completing 30 PCR cycles, 5 μL of each reaction was used as target for an additional 5 cycles of PCR (50 μL total reaction volume) using the HBV surface antigen gene specific oligonucleotide primers C and E (see Table 1, prepared as in Example 2 with reactive pair members) which hybridize with the target at a site adjacent (but not overlapping) the site where the 3' terminus of the primary primers A and B would be if hybridized to the same strands. The final oligonucleotide concentration was 1 μM each. The 203 bp PCR products with reactive pair members at each end of the double-stranded DNA molecules were detected by a microparticle immunoassay performed on a prototype of the Abbott $IM_x$® analyze system using anti-fluorescein coated microparticles and an anti-biotin:alkaline phospatase detection conjugate. Results were:

| No. of molecules | Signal |
| --- | --- |
| 0 | 8.2 |
| $10^2$ | 11.6 |
| $10^3$ | 106.7 |
| $10^4$ | 611.8 |
| $10^5$ | 984.2 |
| $10^6$ | 1100.4 |

Example 5

Single Nested Capture Primer

Two reactions containing 1 μL of a DNA solution with either 0 or $10^5$ HBV plasmid DNA molecules per μL was used as a target for 30 cycles of PCR with HBV surface antigen gene specific primary oligonucleotide primers A and F (See Table 1), primer F being prepared as in Example 2 with a single reactive pair member. Final oligonucleotide concentration was 1 μM each. PCR reaction conditions were identical to those described in Example 4 above.

After completing 30 PCR cycles, 5 μL of each reaction was used as a target for an additional 5 cycles of PCR using the HBV surface antigen gene specific oligonucleotide primers C and F (see Table 1, prepared as in Example 2 with reactive pair members). The final oligonucleotide concentration was 1 μM each. The 440 bp double labeled DNA products were detected as described in Example 2. The result was:

| No. of molecules | Signal |
| --- | --- |
| 0 | 36.2 |
| $10^5$ | 225.3 |

Example 6

Directly Labeled Primers

Synthesis of direct label 4-(2-carboxy-1-ethyl)-7-hydroxy-2-oxo-2H-1-Benzopyran was synthesized according to the procedure described below and shown schematically in FIG. 8 (through structure 5) . The procedure is described in detail in commonly owned, copending application serial no. 07/394,052, filed Aug. 17, 1989, (Attorney Docket No. D-17323), which is incorporated herein by reference. In each of the following cases, R represents Hydrogen.

Figure 8:
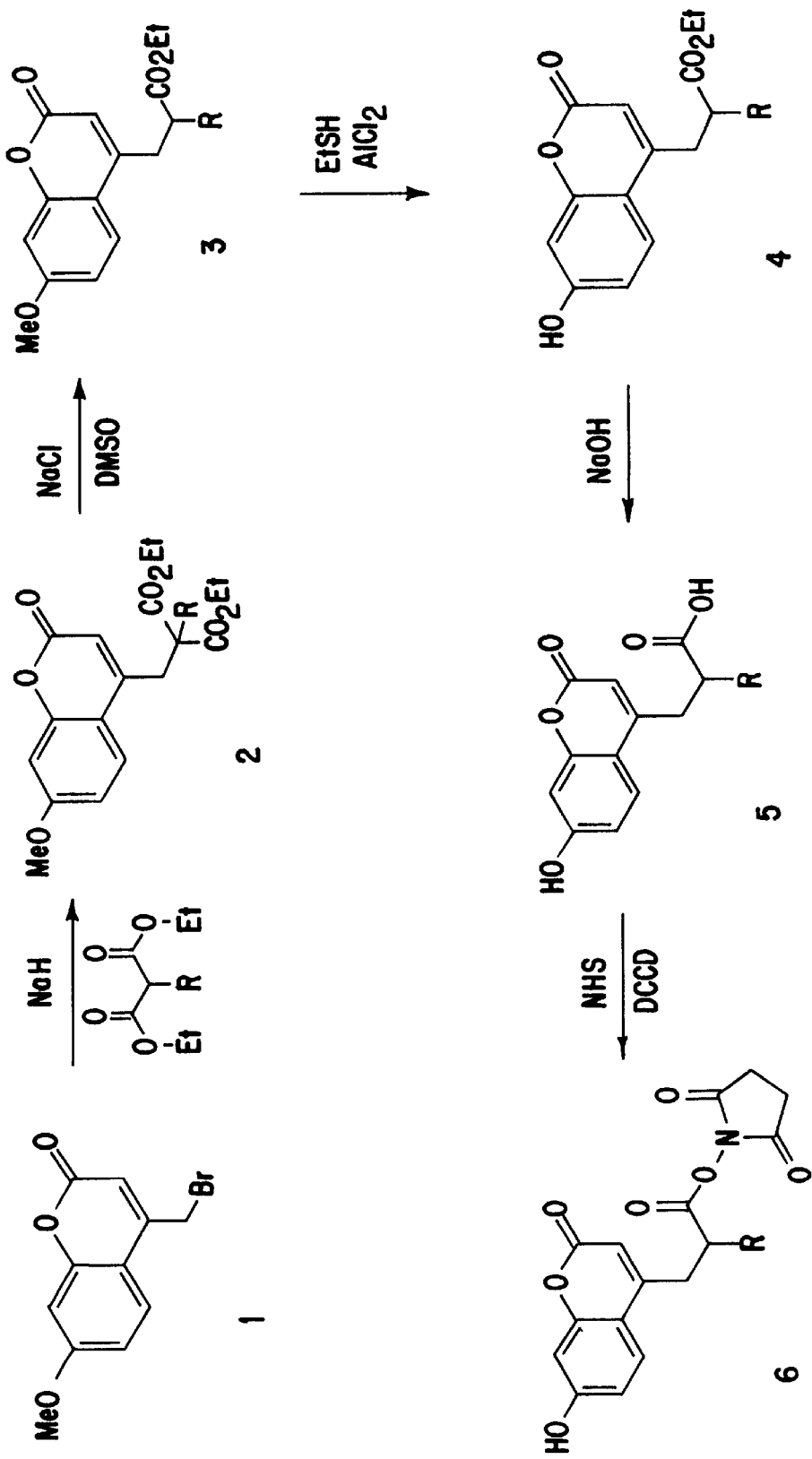
FIG. 8 is a reaction scheme showing the synthesis and coupling of a direct label as described in Example 6.

Referring to FIG. 8 and to structure numbers shown there, 4-bromomethyl-7-methoxycoumarin (1) (Aldrich Chemicals) was converted to 4-(2-bis(carbethoxy)-1-ethyl) -7-methoxy-2-oxo-2H-1-Benzopyran (2) as follows. To a suspension of 240 mg of 60% NaH mineral oil dispersion (6 mmol) in 10 mL of DMF was added 961 μL (6 mmol) of diethyl malonate. After the foaming subsided and the suspension cleared to a solution, 1346 mg (5 mmol) of 4-bromomethyl-7-methoxycoumarin (1), was added all at once. After stirring for 4 h at room temperature, the DMF was stripped off, and the residue partitioned between 0.01M HCl/hexane. The organic phase was concentrated and vacuum dried, then as much as possible was taken up into 4 mL of 50/50 EtOAc/hexane.

To a solution of 44.8 mg (0.13 mmol) of 4-(2-bis (carbethoxy)-1-ethyl)-7-methoxy-2-oxo-2H-1-Benzopyran (2) in 6 mL of DMSO was added 15 mg of NaCl, followed by 4.6 mL of water. The reaction was stirred in an oil bath at 180° C. for 2.5 h, and was cooled to room temperature. After addition of 45 mL of water to the reaction mixture, the resultant emulsion was extracted with 2×40 mL EtOAc. The organic phase was concentrated by rotary evaporation, and was vacuum dried. After uptake into 3 mL of 25% EtOAc in hexane, flash chromatography using the same solvent system gave 31.4 mg of 4-(2-carbethoxy-1-ethyl)-7-methoxy-2-oxo-2H-1-Benzopyran (3), 88%.

To a suspension of 726 mg (5.4 mmol) of $AlCl_3$ in 10 mL of dichloromethane at 0° C. was added 4 mL of EtSH. The suspension became a clear solution within seconds. Then, 298 mg (1.08 mmol) of (3) in 4 mL of dichloromethane was added, turning the yellow solution red in color. The ice bath was removed, and the reaction stirred to room temperature for 3 h. The solvents were removed in vacuo, and the residue thoroughly vacuum dried. The residue was extracted into EtOAc as much as possible, then the extract was flash chromatographed using 30/70 EtOAc/hexane. The long- and short-wave UV active band gave 76.7 mg (27%)of 4-(2-carbethoxy-1-ethyl)-7-hydroxy-2-oxo-2H-1-Benzopyran (4)

A 36.7 mg sample of ester (4)was suspended into 10 mL of water, and 25 mL of 50% aqueous NaOH was added. The resultant solution was stirred at room temperature for 4 h. TLC analysis (30/70 EtOAc/hexane) after this time showed that no starting material remained. The mixture was acidified using 1 mL of 1M HCl. A precipitate formed upon acidification, and the white solid was left to deposit for 1 h. After the solid was filtered off and thoroughly washed with 1M HCl, it was vacuum dried to give 14.1 mg (43%) of analytically pure 4-(2-carboxy-1-ethyl)-7-hydroxy-2-oxo-2H-1-Benzopyran (5).

Direct Labelling of Primers 4-(2-carboxy-1-ethyl)-7-hydroxy-2-oxo-2H-1-Benzopyran (5) was activated to 4-(2-carboxy-1-ethyl)-7-hydroxy-2-oxo-2H-1-Benzopyran, N-hydroxy succinimide ester (6). as follows: To a suspension of (5) in 6 mL of MeCN was added 4.7 mg (41 mmol) of N-hydroxysuccinimide, 8.4 mg (41 mmol) of dicyclohexylcarbodiimide (DCCD) and 2 mg of 4,4-dimethylaminopyridine. The rection was stirred at room temperature for 24 h, and the solvent was removed in vacuo. The residue was taken up into 750 μL of DMF. Thereafter, (6) was directly coupled with the antisense PCR primer, 5'—NH$_2$—GCGGTATAAAGGGACTCACGATGCTGTAC AGACTT-3'. The resulting labelled oligonucleotide was purified, in 14% yield, in identical fashion to the primers containing a member of a reactive pair (See Example 2 above).

PCR and Detection of Labeled Primers

PCR was run using 100 pmol of each primer and 40 attomoles (i.e. 40×10$^{-18}$ mole) of HBV target. After addition of 0.5 units T$_{aq}$ polymerase and 2 nmol of the essential nucleotide triphosphates to a total volume of 100 μL, the reaction was cycled for 1 min at 95° C. (denature), 2 min at 50° C. (anneal), and 2 min at 74° C. (primer extension) After 30 cycles, the microfuge tubes were left at 4° C. Agarose gel electrophoresis showed that the PCR generated a double-stranded product DNA band. With no added target, the PCR did not proceed.

The automated detection of double labeled PCR product was accomplished using antifluorescein-coated latex microparticles for capture and fluorescence detection as the readout. The antifluorescein was covalently coupled to carboxylated latex microparticles using EDAC. The fluorescence detection of microparticle-captured, coumarin-labeled, double-stranded product was done on a breadboard version of the IM$_x$® analyzer (Abbott Laboratories, IL) with modified software. The coumarin-labeled PCR primer possessed an excitation maximum at 378 nm, with an emission maximum at 460 nm. These maxima are well within the wavelength detection ranges for the IM$_x$® analyzer. The protocol for the automated capture/fluorescence readout on the instrument is as follows: A 35 μL sample of PCR product was diluted to 100 μL using ammonium carbonate buffer at pH 9. Then, 35 μL of solution was incubated with 75 μL of antifluorescein-linked microparticles (0.1% solid v/v) at 37° C. for 10 min. After dispensing 100 μL of the incubation solution onto a fiberglass matrix and washing with ammonium carbonate buffer at pH 9, the signal on the microbeads was spectrophotometically determined and recorded as:

| PCR Product | counts* |
| --- | --- |
| Fluorescein-Coumarin | 417 |
| Fluorescein-Biotin | 388 |
| Fluorescein-No label | 379 |

*NOTE: The units of the signal in this example are counts, because the coumarin label is always present and is not generated by an enzyme. In all previous cases, the signal units are counts/sec/sec, which is a rate. This is because the fluorescent moiety was generated by alkaline phosphatase, and it is the rate of this enzyme which is determined.

Example 7

Non-Instrument Detection

Figure 6:
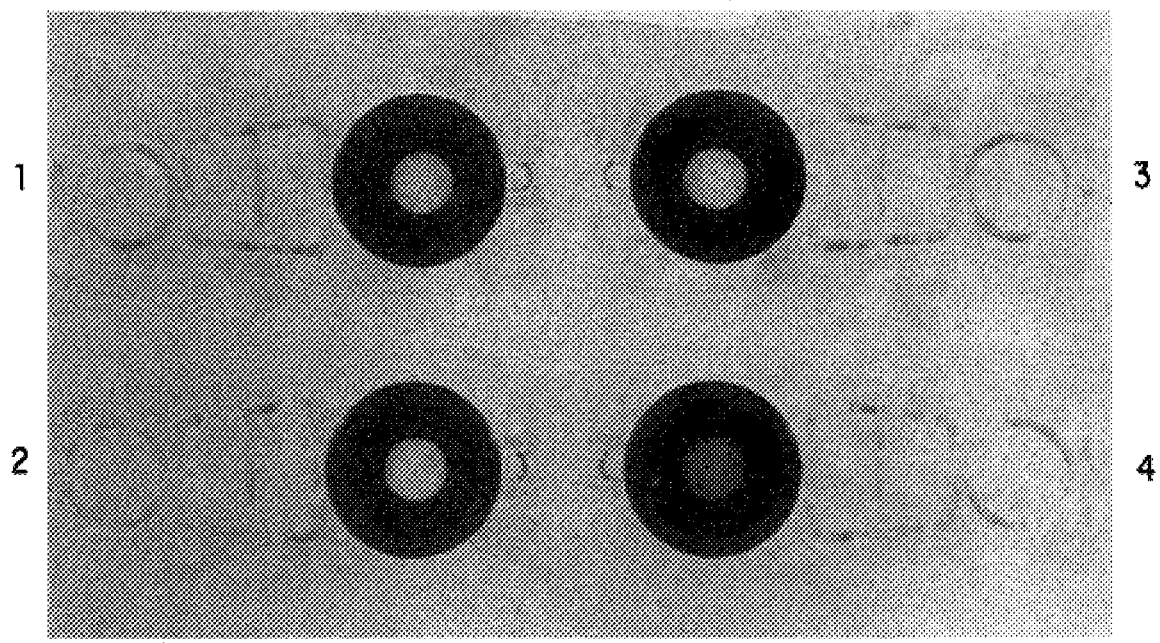
FIG. 6 is photoprint of the results of a non-instrument read assay, wherein the probes at top left contained neither biotin nor fluorescein, at top right, biotin only, at bottom left, fluorescein only, and at bottom right, both biotin and fluorescein.

Four different double-stranded PCR products, produced as in Example 3, were presented for detection by a microparticle immunoassay procedure. One PCR product contained no haptens (derived from primers B and G); another contained only fluorescein hapten (derived from primers B and C); a third contained only biotin hapten (derived from primers F and G); and the fourth contained both a fluorescein and a biotin hapten (derived from primers C and F). These PCR products were incubated with anti-fluorescein coated microparticles and were captured on IM$_x$® analyzer wedges. Anti-biotin:alkaline phosphatase conjugate was added, and bound product was visualized by the addition of nitro blue tetrazolium/5-bromo-4-chloro-3-indolyl phosphate. Only the wedge trapping PCR product containing both fluorescein and biotin exhibited visible blue color (See FIG. 6).

Example 8

Immunochromatographic Detection

Figure 7:
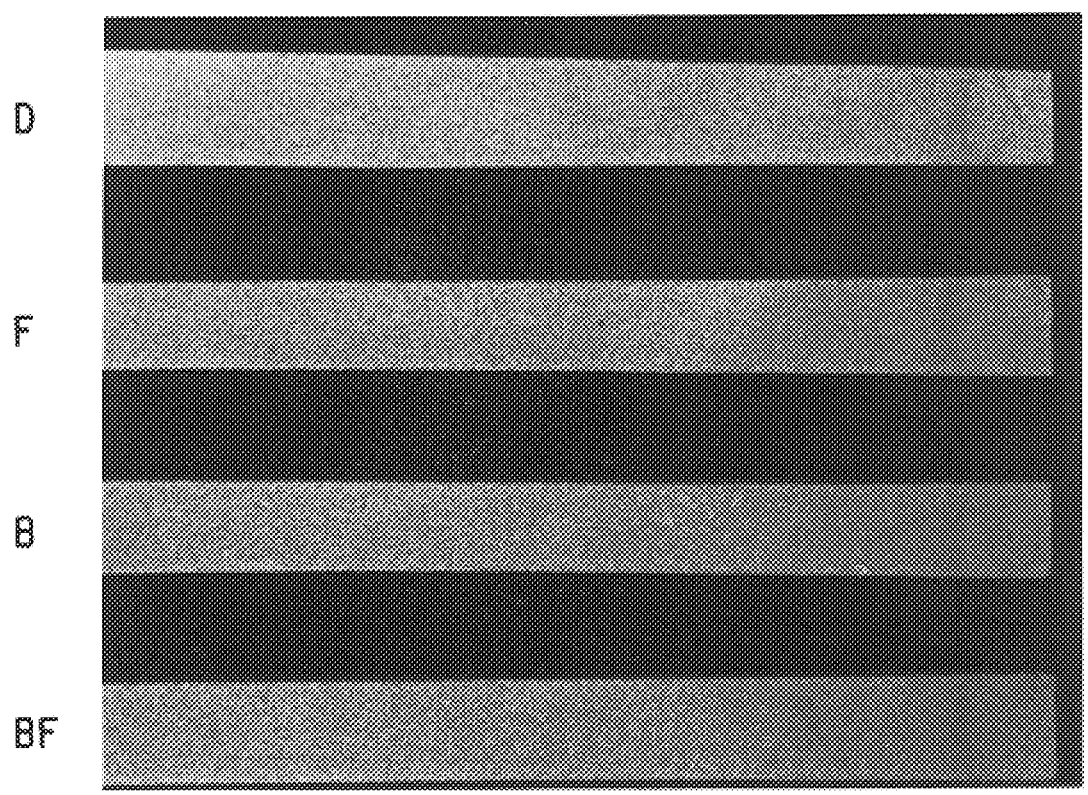
FIG. 7 is a photoprint of an immunochromatographic assay, wherein the probes on strip O contained neither biotin nor fluorescein, on strip F, fluorescein only, on strip B, biotin only, and on strip BF, both biotin and fluorescein.

Four different double-stranded PCR products, produced as in Example 7, were presented for detection by an immunochromatographic technique as taught in publication EP 299 428. The PCR products were incubated with a suspension comprising anti-biotin-conjugated colloidal selenium dispersed in a solution of 150 mM NaCl, 100 mM TRIS, 2% alkali-treated casein, pH 7.4, for about 10 seconds. Into this suspension was dipped a strip of nitrocellulose (approx. 0.4×4.8 cm) onto which had been spotted, approx. 1 cm from the lower end, anti-fluorescein at a concentration of 0.2 mg/mL. As capillary action caused the suspension to migrate up the strip, the anti-biotin:selenium complex was retained on the strip only when both biotin and fluorescein were present on the PCR product (See FIG. 7).

Example 9

Spectrophotometric Detection

Three different PCR products, produced as in Example 3, were presented for detection by a solid-phase enzyme immunoassay system using anti-fluorescein coated ¼ inch polystyrene beads and an anti-biotin:alkaline phosphatase conjugate. One of these PCR products contained only biotin hapten; another only fluorescein hapten; and the third both biotin and fluorescein. Signal was measured using a Quantum® spectrophotometer (Abbott Laboratories).

| PCR product | Signal |
| --- | --- |
| Biotin only | 0.133 |
| Fluorescein only | 0.161 |
| Biotin and Fluorescein | 0.565 |

Example 10

Short PCR for HSV Target

The primers shown in Table 2, below, were synthesized according to a procedure substantially the same as the procedure described in Example 1, and were labeled at their 5' ends substantially as described in Example 2. The target sequence was Herpes Simplex Virus (HSV) HSV-1 and/or HSV-2. The map position is according to McGeoch, D. J. et al. *J. Gen. Virol.* 68:19–38 (1987). Primers H and I are specific for HSV-2 while primers J and K are consensus sequences which will detect both HSV-1 and HSV-2.

TABLE 2

| | MAP POS | Hapten | SEQUENCE |
| --- | --- | --- | --- |
| H | 4752–4774 | FL- | CCCCCTGTTC TGGTTCCTAA CGG |
| I | 4775–4797 | BIOTIN- | GAGGATATCT AGAGCAGGGG AGG |
| J | 6466–6488 | FL- | TATGACAGCT TTAGCGCCGT CAG |
| K | 6489–6511 | BIOTIN- | TCAGGAACCC CAGGTTATCC TCG |

HEp2 cultures were obtained known to have HSV-1 DNA present (ie. those designated R+R, 5082 and 5123); other cultures were known to contain HSV-2 DNA (ie. those designated 316 and 196). Noninfected HEp2 samples were used as controls. PCR was run using primer set J,K at $2 \times 10^{12}$ molecules and H,I at $0.75 \times 10^{12}$ molecules in 100 μL total volume (10 μL sample) for 25 cycles of: 94° C.×1 min., 50° C.×1 min., and 72° C.×2 min. Taq polymerase was used at 2.5 units per reaction. The product was isolated and detected in an $IM_x$® analyzer instrument as described above. The average results of duplicate runs are given below.

| | Rate (counts/sec/sec) | |
| --- | --- | --- |
| Sample | Consensus Primers J & K | HSV-2 Specific Primers H & I |
| Hep2 (control) | 7.56 | 8.57 |
| R + R (HSV-1) | 1591.32 | 9.73 |
| 5082 (HSV-1) | 408.08 | 8.25 |
| 5123 (HSV-1) | 1563.43 | 9.37 |
| 316 (HSV-2) | 1604.28 | 1119.75 |
| 196 (HSV-2) | 1349.24 | 868.73 |

Other modifications will be apparent to those of ordinary skill in the art. Such modifications are to be included within the scope of the present invention unless the claims which follow expressly state otherwise.

What is claimed is:

1. A method for amplifying and detecting a target nucleic acid sequence in a sample, comprising:
    a) hybridizing to each of the target and its complementary strand respective oligonucleotide primers, wherein one primer, a capture primer, is conjugated to a first member of a specific binding pair and the other primer, a labeled primer, is conjugated directly to a detectable moiety or to a first member of a second specific binding pair capable of specifically reacting with a detectable moiety;
    b) synthesizing from each primer an extension product complementary to each nucleic acid strand, the extension product of each primer forming a template for the synthesis of extension products from the other primer once the extension product is separated from its complement;
    c) separating the primer extension products from the templates on which they were synthesized to produce single-stranded molecules;
    d) treating the single-stranded molecules generated from step (c) with the primers of step (a) under conditions that a primer extension product is synthesized using each of the single strands produced in step (c) as templates to foil double-stranded products containing said capture primer and said labeled primer;
    e) capturing said double-stranded products from step (d) on a solid phase having associated therewith the other member of said specific binding pair so that said double-stranded products become linked to said solid phase by said specific binding pair, thereby associating said labeled primer with said solid phase; and
    f) detecting said labeled primer associated with said solid phase as a measure of the target nucleic acid in the sample.

2. The method of claim 1 wherein the labeled primer of step (a) is directly conjugated to a detectable moiety.

3. The method of claim 1 wherein the labeled primer of step (a) is conjugated to a first member of a second specific binding pair, the second member of said second specific binding pair being conjugated to a detectable moiety, and wherein prior to step (f) the method further comprises treating said double stranded products with said second member of said second specific binding pair.

4. The method of claim 3 wherein the capture primer is conjugated to a first specific binding pair which does not specifically bind the first member of said second specific binding pair conjugated to the labeled primer.

5. The method of claim 3 wherein said specific binding pairs are different.

6. The method of claim 3 wherein said specific binding pairs are selected from the group consisting of antibody and antigen, biotin and avidin, enzyme and enzyme receptor, carbohydrate and lectin, biotin and antibiotin, and pairs of complementary DNA strands.

7. The method of claim 3 wherein each of said primers is linked at its 5' end to its specific binding pair member.

8. The method of claim 1 wherein steps (c) and (d) are repeated at least once.

9. A method for further amplifying and detecting amplified, double stranded target nucleic acid sequences in a sample, comprising:
    a) hybridizing to the complementary amplified target strands a pair of secondary oligonucleotide primers, each of said secondary primers being linked to first members of different first and second specific binding pairs, respectively;
    b) synthesizing from each secondary primer extension products complementary to the target nucleic acid strands, the extension product of each primer forming a template for the synthesis of extension products from the other primer once the extension product is separated from its complement;
    c) separating the primer extension products from the templates on which they were synthesized to produce single-stranded molecules;
    d) treating the single-stranded molecules from step (c) with the primers of step (a) under conditions that a primer extension product is synthesized using the single strands in step (c) as templates to form double-stranded products;

e) capturing said double-stranded products from step (d) on a solid phase having associated therewith a second member of said first specific binding pair, so that said double stranded products become linked to said solid phase by said first specific binding pair; and f) before, during or after step (e), treating said double-stranded products of step (d) with detectable second members of said second specific binding pair, said second members being reactive with the first member of said second specific binding pair on said double-stranded products to link therewith; and g) detecting the detectable second members associated with said solid phase as a measure of the target nucleic acid in the sample.

10. The method of claim 9 wherein a first amplification is performed by PCR using a pair of primary oligonucleotide primers.

11. The method of claim 10 wherein each of said secondary primers hybridizes to an amplified extension product at a site 3' to the hybridization site of the primary primer.

12. The method of claim 9 wherein steps (c) and (d) are repeated at least once.

13. The method of claim 9 wherein the second member of said second specific binding pair does not specifically bind the first or second members of said first specific binding pair.

14. The method of claim 9 wherein said specific binding pairs are selected from the group consisting of antibody and antigen, biotin and avidin, enzyme and enzyme receptor, carbohydrate and lectin, biotin and antibiotin, and pairs of complementary DNA strands.

15. In a method for amplifying and detecting target oligonucleotide sequences in a sample where for each target sequence two primary primers are employed, one to hybridize with the target sequence and the other to hybridize with its complement, to form primary extension products complementary to the target and its complement, the primary extension products forming templates for the synthesis of further primary extension products from the primary primers, the improvement comprising:

during or after the reaction of the primary primers and target sequence, treating the primary extension products with at least one additional secondary primer, said secondary primer being linked to a first member of a specific binding pair, at least one of said secondary primers being hybridizable with one of the primary extension products at a site 3' to a primary primer's terminus to form secondary extension products;

capturing any such secondary extension products on a solid phase having associated therewith the second member of said specific binding pair; and detecting whether secondary extension products are formed as a measure of the target oligonucleotide sequences in the sample.

16. The method of claim 15 wherein said primary extension products are treated with at least two secondary primers, one secondary primer being linked to a first member of a first specific binding pair, and a second secondary primer being linked to a first member of a second specific binding pair.

17. The method of claim 16 wherein the first member of at least one of said first and second specific binding pairs is reactive with a detectable moiety, and said secondary extension products are detected by linking said detectable moiety to said specific binding pair and detecting said detectable moiety.

18. The method of claim 15 wherein at least one of said primary primers is linked to a member of a second specific binding pair.

19. The method of claim 18 wherein said one primary primer and said one secondary primer are linked at their respective 5' ends to their respective specific binding pair members.

20. In a method for amplifying and detecting target oligonucleotide sequences in a sample where for each target sequence at least two primers are employed, one to hybridize with the target sequence and the other to hybridize with its complement to form extension products complementary to the target and its complement, the extension products forming templates for the synthesis of further extension products from the primers, wherein one of the primers, a labeled primer, is labeled for detection, the improvement comprising: linking at least the other of said primers, a capture primer, to a first member of a specific binding pair, separating said extension products from said sample with a solid phase having associated therewith the second member of said specific binding pair, and detecting the labeled primer as a measure of the target oligonucleotide sequences in the sample.

21. The method as recited in claim 20 further comprising providing the labeled primer with a detectable label linked directly to it whereby said extension products separated with said solid phase can be detected with said label.

22. The method of claim 21 wherein said specific binding pair is selected from the group consisting of antibody and antigen, biotin and avidin, carbohydrate and lectin, and enzyme and enzyme receptor.

23. The method of claim 22 wherein the detectable label is selected from a group consisting of a chromophore, a fluorophore and a chemilumophore.

24. A kit for amplifying and detecting a target nucleic acid sequence, comprising:

at least two primers, one primer complementary to said target sequence, and the other primer complementary to the target-complementary sequence wherein primer extension products can be synthesized from said primers such that each extension product forms a template for the synthesis of further extension products from the primers and wherein at least one of said primers has a first member of a specific binding pair linked to it and the other primer is labeled with a detectable moiety;

a DNA polymerase; and a solid phase having linked thereto the second member of said specific binding pair which can bind to said first member on said one primer.

25. The kit as recited in claim 24 wherein the other primer is linked to a first member of a second specific binding pair.

26. The kit of claim 25 further including a conjugate which includes a detectable moiety linked to the second member of said second specific binding pair.

27. The kit of claim 24 wherein the other primer is linked directly to a detectable label.

28. The kit of claim 24 including two pairs of said primers for each target sequence, one pair nested within the other.

29. The kit of claim 28 wherein one of said nested primers is linked with said first member of a specific binding pair, and the other nested primer is linked with a first member of a second specific binding pair, said kit further including a conjugate of a detectable moiety linked to the second member of said second specific binding pair.

30. The kit of claim 24 further including a third primer nested between said two primers, said third primer being linked to a first member of a second specifc binding pair.

31. The method of claim 1 wherein primers are selected such that, during steps (a) and (d) when primers are hybridized to target or its complementary strand or to extension products, the 3' terminus of the capture primer hybridizes to one strand at a position which is substantially opposite the position on the complementary strand at which the 3' terminus of the labeled primer hybridizes.

32. The method of claim 31 wherein the primers are selected such that the 3' terminus of each primer hybridizes to its respective strand at a position one base short of the position on the opposite strand where the other primer hybridizes.

33. The method of claim 1 wherein each primer comprises from about 15 to about 50 deoxyribonucleotides.

34. A method for making and detecting a target nucleic acid amplification product, comprising:
   a) hybridizing to each of the target and its complementary strand respective oligonucleotide primers, wherein one primer, a capture primer, is conjugated to a first member of a first specific binding pair and the other primer, a labeled primer, is conjugated directly to a detectable moiety or to a first member of a second specific binding pair capable of specifically reacting with a detectable moiety;
   b) synthesizing from each primer an extension product complementary to each nucleic acid strand, the extension product of each primer being used in the synthesis of further extension products from the other primer once the extension product is separated from its complement;
   c) separating the extension products from the templates on which they were synthesized to produce single-stranded molecules;
   d) treating the single-stranded molecules generated from step (c) with the primers of step (a) under conditions that an extension product is synthesized using the single strands produced in step (c) to form double-stranded products containing said capture primer and said labeled primer;
   e) capturing said double-stranded products from step (d) on a solid phase having associated therewith the other member of said first specific binding pair so that said double-stranded products become attached to said solid phase by said specific binding pair, thereby associating said labeled primer with said solid phase; and
   f) assaying said labeled primer associated with said solid phase as a measure of the amplification product.

35. The method of claim 34 wherein the labeled primer of step (a) is directly conjugated to a detectable moiety.

36. The method of claim 34 wherein the labeled primer of step (a) is conjugated to a first member of a second specific binding pair, the second member of said second specific binding pair being conjugated to a detectable moiety, and wherein prior to step (f) the method further comprises treating said double stranded products with said second member of said second specific binding pair.

37. The method of claim 36 wherein said specific binding pairs are selected from the group consisting of antibody and hapten, biotin and avidin, enzyme and enzyme receptor, carbohydrate and lectin, and pairs of complementary DNA strands.

38. The method of claim 36 wherein each of said primers is linked at its 5' end to its specific binding pair member.

39. The method of claim 34 wherein primers are selected such that, during steps (a) and (d) when primers are hybridized to target or its complementary strand or to extension products, the 3' terminus of the capture primer hybridizes to one strand at a position which is substantially opposite the position on the complementary strand at which the 3' terminus of the labeled primer hybridizes.

40. The method of claim 39 wherein the primers are selected such that the 3' terminus of each primer hybridizes to its respective strand at a position one base short of the position on the opposite strand where the other primer hybridizes.

* * * * *